US011419807B2

(12) United States Patent
Aubrun et al.

(10) Patent No.: US 11,419,807 B2
(45) Date of Patent: Aug. 23, 2022

(54) COSMETIC COMPOSITION FOR KERATIN FIBRES

(71) Applicant: L'OREAL, Paris (FR)

(72) Inventors: Odile Aubrun, Chevilly Larue (FR); Stephane Douezan, Chevilly Larue (FR); Mohamed Boularas, Chevilly Larue (FR); Maitena Leuridan, Chevilly Larue (FR); Philippe Ilekti, Chevilly Larue (FR)

(73) Assignee: L'OREAL, Paris (FR)

( * ) Notice: Subject to any disclaimer, the term of this patent is extended or adjusted under 35 U.S.C. 154(b) by 17 days.

(21) Appl. No.: 17/048,008

(22) PCT Filed: Apr. 16, 2019

(86) PCT No.: PCT/EP2019/059817
§ 371 (c)(1),
(2) Date: Oct. 15, 2020

(87) PCT Pub. No.: WO2019/201930
PCT Pub. Date: Oct. 24, 2019

(65) Prior Publication Data
US 2021/0106514 A1 Apr. 15, 2021

(30) Foreign Application Priority Data
Apr. 16, 2018 (FR) ...................... 18 53293

(51) Int. Cl.
| A61Q 1/10 | (2006.01) |
| A61K 8/65 | (2006.01) |
| A61K 8/34 | (2006.01) |
| A61K 8/41 | (2006.01) |
| A61K 8/81 | (2006.01) |

(52) U.S. Cl.
CPC ............... *A61K 8/65* (2013.01); *A61K 8/345* (2013.01); *A61K 8/41* (2013.01); *A61K 8/8182* (2013.01); *A61K 2800/43* (2013.01)

(58) Field of Classification Search
CPC ...... A61Q 5/065; A61Q 1/10; A61K 2800/43; A61K 8/342; A61K 8/42; A61K 8/34; A61K 8/37; A61K 8/92; A61K 8/65; A61K 8/41; A61K 8/345
USPC ....................................................... 424/70.1
See application file for complete search history.

(56) References Cited

U.S. PATENT DOCUMENTS

| 3,915,921 | A | 10/1975 | Schlatzer, Jr. |
| 5,156,911 | A | 10/1992 | Stewart |
| 5,519,063 | A | 5/1996 | Mondet et al. |
| 5,614,200 | A | 3/1997 | Bartholomey et al. |
| 6,090,395 | A | 7/2000 | Asmus et al. |
| 6,461,597 | B1* | 10/2002 | Morita ..................... A61Q 5/00 424/70.1 |
| 6,534,069 | B1 | 3/2003 | Asmus et al. |
| 2004/0185070 | A1 | 9/2004 | Barrow et al. |
| 2005/0265941 | A1 | 12/2005 | Mateu et al. |
| 2007/0014744 | A1 | 1/2007 | Swistowski et al. |
| 2007/0202069 | A1* | 8/2007 | Tamareselvy .......... A61Q 19/00 424/70.12 |
| 2008/0207778 | A1 | 8/2008 | Rodier et al. |
| 2009/0196842 | A1* | 8/2009 | Zech ........................ A61Q 5/06 424/70.7 |
| 2010/0129305 | A1 | 5/2010 | Lee et al. |
| 2012/0093896 | A1* | 4/2012 | Mongiat ................ A61Q 19/00 424/401 |
| 2013/0295035 | A1 | 11/2013 | Sugimoto et al. |
| 2014/0093467 | A1 | 4/2014 | Knappe et al. |
| 2015/0079016 | A1 | 3/2015 | Bolognini et al. |
| 2015/0125403 | A1* | 5/2015 | Joerger ................ A23K 20/105 424/49 |
| 2015/0174056 | A1 | 6/2015 | Barba et al. |
| 2015/0335566 | A1 | 11/2015 | Knappe et al. |
| 2016/0143827 | A1* | 5/2016 | Castan Barberan ..... A61K 8/42 424/70.1 |
| 2016/0263010 | A1* | 9/2016 | Abdo ....................... A61K 8/89 |
| 2017/0035679 | A1 | 2/2017 | Douezan et al. |
| 2017/0354588 | A1 | 12/2017 | Sortino et al. |
| 2017/0367950 | A1 | 12/2017 | Terrisse et al. |

FOREIGN PATENT DOCUMENTS

| DE | 102 44 117 A1 | 4/2004 |
| DE | 10 2005 033 520 A1 | 1/2007 |
| DE | 10 2011 077 364 A1 | 12/2012 |
| EP | 1 001 759 | 5/2000 |
| EP | 1 407 755 A1 | 4/2004 |
| EP | 1 933 806 A1 | 6/2008 |
| EP | 2 686 070 A2 | 1/2014 |
| EP | 2 686 070 B1 | 3/2018 |
| FR | 3 031 298 A1 | 7/2016 |

(Continued)

OTHER PUBLICATIONS

International Search Report dated Jun. 26, 2019 in PCT/EP2019/059817 filed on Apr. 16, 2019, 4 pages.

(Continued)

*Primary Examiner* — Eisa B Elhilo
(74) *Attorney, Agent, or Firm* — Oblon, McClelland, Maier & Neustadt, L.L.P.

(57) ABSTRACT

Composition, preferably a cosmetic composition, for caring for and/or making up keratin materials, preferably the eyelashes and/or the eyebrows, comprising: —(1) at least one linear fatty acid monoester of formula (I): $R_1$—O—$R_2$ in which $R_1$ and $R_2$ are linear and saturated and have, independently of one another, a number of carbon atoms greater than or equal to 20, with $R_1$ representing an acyl radical, and $R_2$ representing an alkyl radical, and —(2) at least one fatty acid having from 14 carbon atoms to less than 20 carbon atoms, —(3) at least one organic base, in particular derived from an alkanolamine, capable of at least partially neutralizing at least one fatty acid (2), and —(4) at least one fatty alcohol preferably chosen from $C_{14}$-$C_{30}$ fatty alcohols, better still chosen from the linear and saturated $C_{14}$-$C_{24}$, even better still $C_{14}$-$C_{20}$, fatty alcohols, and —(5) water.

25 Claims, No Drawings

(56) References Cited

FOREIGN PATENT DOCUMENTS

| WO | WO 98/11887 A2 | 3/1998 |
| WO | WO 2007/042723 A1 | 4/2007 |
| WO | WO 2017/218530 A1 | 12/2017 |

OTHER PUBLICATIONS

French Preliminary Search Report (with translation of categories) dated Nov. 19, 2018 in French Application No. 18 53287 filed on Apr. 16, 2018, 4 pages.
French Preliminary Search Report (with translation of categories) dated Nov. 15, 2018 in French Application No. 18 53292 filed on Apr. 16, 2018 3 pages.
French Preliminary Search Report (with translation of categories) dated Nov. 22, 2018 in French Application No. 18 53290 filed on Apr. 16, 2018 3 pages.

\* cited by examiner

COSMETIC COMPOSITION FOR KERATIN FIBRES

The present invention relates to the field of caring for and/or making up keratin materials, and is directed towards proposing compositions more particularly intended for making up the eyelashes or the eyebrows.

The term "keratin materials" is preferably intended to mean human keratin materials, especially keratin fibres.

The term "keratin fibres" is in particular intended to mean the eyelashes and/or the eyebrows, and preferably the eyelashes. For the purposes of the present invention, this term "keratin fibres" also extends to synthetic false eyelashes.

In general, compositions intended for making up keratin fibres, for example the eyelashes, aim to densify the thickness and the visual perception of the eyelashes and ultimately the gaze. These mascaras are described as aqueous or else cream mascaras, when they are formulated in an aqueous base, and anhydrous mascaras when they are formulated as a dispersion in an organic solvent medium.

A great diversity of cosmetic effects can be provided by the application of a mascara to keratin fibres and in particular the eyelashes, for instance a volumising, lengthening, thickening and more particularly charging makeup effect.

These effects are mostly adjusted through the amount and nature of the particles and most particularly those of the waxes present in the mascaras. In general, mascaras in fact have a significant amount of wax(es) and in particular from 10% to 35% by weight of wax(es), more generally from 15% to 30% by weight, relative to the total weight thereof.

For obvious reasons, improving the textures of mascara which condition the manifestation of one or more makeup effects is a constant preoccupation of those producing cosmetic formulations.

Moreover, the specific effects associated with a particular formulation, for example charging and moreover providing excellent separation of the eyelashes made up, are expected to be reproduced virtually identically by all the production batches of one and the same formulation.

In order to meet these expectations and/or objectives, it is therefore necessary to be capable of precisely adjusting the texture of a mascara and of reproducing it as faithfully as possible with batches that are not necessarily produced at the same time but which are identical in terms of ingredients and must therefore provide makeup effects that are in theory also identical.

However, as specified above, most of the mascaras currently available are formulated with a significant amount of waxes. In point of fact, as detailed in the document Ullmann's Encyclopedia of Industrial Chemistry 2015, Wiley-VCH Verlag GmbH & Co. KGaA, Weinheim 10.1002/14356007.a28.pub2, most waxes are not constituted of a single chemical compound, but are instead complex mixtures. They may be mixtures of oligomers and/or of polymers which, in many cases, also have varied molar masses, varied molar mass distributions and also varied degrees of branching. Thus, a polar wax is conventionally made up of a mixture of alkanes, fatty alcohols and fatty esters, the fatty-chain length of which varies according to the melting point.

It is therefore very difficult for the producers of these waxes to guarantee a rigorously identical composition for all production batches. More specifically, there may be, between several production batches of one and the same wax, a variability in terms of the chemical nature of some of its constituent compounds. Likewise, the proportionality of some of its constituent compounds may also vary between production batches.

For obvious reasons, these variabilities have a not insignificant impact on the properties of the wax and therefore on those of the mascara incorporating this wax in significant amount. Thus, two mascara formulations of identical composition and therefore produced from one and the same conventional wax in the same amount, can nevertheless diverge in terms of rheological properties and therefore of texture, if they were produced from two separate production batches of this wax.

Consequently, the use of conventional waxes, in particular in significant amount, in mascara compositions does not make it possible to guarantee for users the reproduction of finely adjusted and totally identical rheo logical properties in all the mascara specimens of one and the same composition.

The present invention aims precisely to provide mascara compositions which have dispensed with this limitation.

Thus, a first objective of the present invention is to obtain mascara compositions of which the texturing properties are finely adjustable and reproducible.

Another objective of the present invention is to provide a mascara architecture produced using a predominant weight proportion of single-component ingredients. The predominant use of single-component ingredients advantageously makes it possible to dispense with the risk of composition variability that may exist between several production batches of a multicomponent ingredient and therefore to dispense with the risk of its impact on the final properties of the mascara.

Another objective of the present invention is to provide a mascara architecture which makes it possible to significantly reduce or even dispense with the use of waxes, but which nevertheless remains very satisfactory in terms of makeup effect.

Thus, another objective of the invention is to provide consumers with compositions, especially cosmetic compositions, and in particular mascaras, that are compatible with a long playtime while at the same time making it possible to preserve the separation of the eyelashes.

Another objective of the invention is to also provide consumers with compositions which have a creamy texture.

Finally, an objective of the invention is to meet, for the most part, the above-mentioned subjects while at the same time providing the composition with great stability.

The term "stable composition" is intended to mean that the composition remains usable as makeup after storage for two months at a temperature of 45° C. and that it retains its pleasantness and its sensory signature on application. More specifically, a "stable composition" according to the invention has an acceptable change in viscosity, that is to say that the difference between the initial viscosity and the viscosity after storage for two months at a temperature of 45° C. remains less than 10 Pa·s.

Unexpectedly, the inventors have noted that it is possible to significantly or even totally dispense with waxes as texturing agent in formulations for making up and/or caring for keratin fibres and therefore with the limitations mentioned above, with the proviso of combining very specific compounds in such formulations.

Thus, according to a first of its aspects, the present invention relates to a composition, preferably a cosmetic composition, in particular for caring for and/or making up keratin materials, in particular the eyelashes, comprising:

(1) at least one linear fatty acid monoester of formula (I):

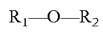

in which $R_1$ and $R_2$ are linear and saturated and have, independently of one another, a number of carbon atoms greater than or equal to 20, with $R_1$ representing an acyl radical, and $R_2$ representing an alkyl radical, and (2) at least one fatty acid having from 14 carbon atoms to less than 20 carbon atoms, (3) at least one organic base, in particular derived from an alkanolamine, capable of at least partially neutralizing at least one fatty acid (2), and (4) at least one fatty alcohol preferably chosen from $C_{14}$-$C_{30}$ fatty alcohols, better still chosen from the linear and saturated $C_{14}$-$C_{24}$, even better still $C_{14}$-$C_{20}$, fatty alcohols, and (5) water.

Unexpectedly, the inventors have in fact noted that the formulation in an aqueous medium of at least one linear fatty acid monoester (1), in combination with at least one neutralized form of a fatty acid having from 14 carbon atoms to less than 20 carbon atoms, (2) and at least one fatty alcohol preferably chosen from $C_{14}$-$C_{30}$ fatty alcohols, better still chosen from the linear and saturated $C_{14}$-$C_{24}$, even better still $C_{14}$-$C_{20}$, fatty alcohols (4), makes it possible to obtain compositions of which the texture can be finely adjusted and guaranteed in terms of reproducibility.

As emerges from what follows, these new compositions are advantageous in several respects.

First of all, the compounds (1) to (4) required according to the invention are of synthetic origin and, in this respect, of increased purity compared for example with a natural wax.

They are also, as individualized compounds, single-component compounds or compounds with a very precise number of components, as opposed to the majority of conventional waxes which are often multicomponent or even have an indefinite number of compounds, such as natural waxes and some synthetic waxes.

These two specificities are particularly advantageous since they make it possible to dispense with a risk of variability with regard to their respective compositions.

As emerges from the examples below, the compositions in accordance with the invention and based on the use of the compounds (1) to (4) as texturing agent prove to be very satisfactory in terms of makeup effects.

Thus, compositions according to the invention may have a creamy texture which proves to be finely adjustable by virtue of the use of the required combination according to the invention.

The obtaining of these properties is conditioned by the use of the compounds (1) to (4) and advantageously does not therefore require the additional presence of waxes, in particular in significant amount.

Thus, the compositions according to the invention advantageously comprise less than 5% of waxes as defined below.

The term "wax" is intended to mean lipophilic compounds, which are solid at ambient temperature (20° C.) and at atmospheric pressure (760 mmHg), with a reversible solid/liquid change of state, which have a melting point of greater than or equal to 40° C., which may range up to 120° C.

For the purposes of the invention, the waxes to which this abovementioned amount limitation relates are distinct from those capable of being embodied by the component which is a monoester of fatty acid(s) (1) and fatty alcohol (4) required according to the invention.

Finally, the manifestation of the makeup effects provided by the combination of the compounds (1) to (4) is not acquired to the detriment of the stability of the compositions.

According to another of its aspects, the present invention relates to a process, in particular a cosmetic process, for caring for and/or making up keratin materials, in particular the eyelashes and/or the eyebrows, comprising at least one step consisting in applying, to said keratin materials, in particular the eyelashes and/or eyebrows, a composition in accordance with the invention.

Fatty Acid Monoester (1)

A composition according to the invention comprises at least one linear fatty acid monoester.

A composition according to the invention may comprise at least 5.0% by weight, preferably at least 6.0% by weight, better still at least 7.0% by weight of fatty acid monoester(s) relative to the total weight of the invention.

According to one particularly preferred embodiment of the invention, the fatty acid monoester(s) are present in the composition in a content ranging from 6.0% to 35.0% by weight, preferably from 7.0% to 30.0%, or even preferably from 8.0% to 28.0% by weight, relative to the total weight of the composition.

The linear fatty acid monoester(s) (1) in question according to the invention correspond to formula (I) below:

$$R_1\text{—}O\text{—}R_2 \qquad (I)$$

in which $R_1$ and $R_2$ are linear and saturated and have, independently of one another, a number of carbon atoms greater than or equal to 20, with $R_1$ representing an acyl radical, and $R_2$ representing an alkyl radical.

This or these fatty acid monoester(s) is (are) used during the preparation of a composition according to the invention, in an individualized form or in the form of a mixture comprising exclusively linear fatty acid monoesters of formula (I).

In one preferred embodiment, the fatty acid monoester(s) has (have) a melting point greater than 50° C.

The melting point may be measured by any known method and in particular using a differential scanning calorimeter (DSC).

According to one preferred embodiment of the invention, the acyl and alkyl radicals representing respectively $R_1$ and $R_2$ are chosen in such a way that the compound (I) is solid at a temperature of less than or equal to 30° C.

According to one particularly preferred embodiment of the invention, $R_1$ and $R_2$ are, respectively, acyl and alkyl radicals having a number of carbon atoms ranging from 20 to 30, preferably from 20 to 24.

According to one particularly preferred embodiment, $R_1$ and $R_2$ are, respectively, acyl and alkyl radicals having the same number of carbon atoms.

In particular, the fatty acid monoester according to the invention is chosen from arachidyl arachidate and behenyl behenate.

According to one particularly preferred embodiment of the invention, the linear fatty acid monoester is a behenyl behenate.

A behenyl behenate suitable for the composition according to the invention may in particular be Kester Wax K-72 sold by the company Koster Keunen, DUB BB sold by the company Stéarinerie Dubois, or Dermowax BB sold by Alzo.

Ionic Surfactant

As specified above, the fatty acid monoester(s) (1) used according to the invention are combined with at least one ionic surfactant resulting from the neutralization of a fatty acid (2) comprising from 14 to less than 20 carbon atoms by an organic base (3).

More specifically, the ionic surfactant in question according to the invention results from the at least partial neutralization of the carboxylic functions of a fatty acid (2) comprising from 14 to less than 20 carbon atoms by an organic base (3).

Fatty Acid (2)

The fatty acid according to the invention comprises from 14 to less than 20 carbon atoms. According to one preferred embodiment of the invention, the fatty acid comprises from 16 to less than 20 carbon atoms. According to one particularly preferred embodiment, the number of carbon atoms ranges from 16 to 18.

In particular, the fatty acid(s) according to the invention is (are) chosen from linear fatty acids, saturated fatty acids and mixtures thereof.

According to one particularly advantageous embodiment of the invention, the fatty acid of the ionic surfactant is linear and saturated.

According to one particular embodiment of the invention, the fatty acid(s) is (are) chosen from palmitic acid, stearic acid and mixtures thereof, and preferably comprises at least stearic acid having the INCI name Stearic Acid.

According to one particularly preferred embodiment of the invention, the composition uses, as fatty acid (2), a mixture of $C_{16}$-$C_{18}$ fatty acids, preferably a mixture of fatty acids having 16 carbon atoms, such as palmitic acid, and of fatty acids having 18 carbon atoms, such as stearic acid.

A preferred stearic acid suitable for the invention is, for example, Stearic Acid 1850 sold by the company Southern Acids.

A composition according to the invention may comprise at least 3.0% by weight of fatty acid(s) (2) relative to the total weight of the composition According to one preferred embodiment of the invention, the fatty acid is present in a content ranging from 3.5% to 20.0% by weight, preferably from 4.0% to 20.0%, better still from 4.5% to 15.0%, even better still from 5.0% to 15.0% by weight of fatty acid (2), in particular of stearic acid, relative to the total weight of the composition.

As mentioned above, this fatty acid is used in an ionic form generated via its interaction with an organic base. This base is used at an amount sufficient to be capable of at least partially neutralizing at least one fatty acid (2).

Organic Base (3)

The composition according to the invention comprises at least one organic base.

The organic base(s) may in particularly be chosen from ammonium, and its amine and amino alcohol derivatives.

Preferably, the base of organic origin is chosen from alkanolamines such as monoethanolamine, diethanolamine, triethanolamine, triisopropanolamine, aminomethylpropanol, tromethamine and aminomethylpropanediol. According to one particular embodiment, the base is a primary (poly)hydroxyalkylamine. The term "primary (poly)hydroxyalkylamine" is intended to mean in particular a primary dihydroxyalkylamine, the term "primary" being intended to mean a primary amine function, i.e. —$NH_2$, and the alkyl group being a linear or branched $C_1$-$C_8$, preferably $C_4$ branched, hydrocarbon-based chain, such as 1,3-dihydroxy-2methylpropyl. The primary (poly)hydroxyalkylamine is preferably 1,3-dihydroxy-2-methyl-2-propylamine (also known as aminomethylpropanediol or AMPD).

According to one preferred embodiment of the invention, the base of organic origin is chosen from triethanolamine, aminomethylpropanol and/or aminomethylpropanediol, and preferably comprises aminomethylpropanediol.

Such an aminomethylpropanediol suitable for the invention is, for example, AMPD Ultra PC sold by the company Angus (Dow Corning).

The amount of organic base is adjusted so as to obtain sufficient neutralization to confer an effective ionicity on the associated fatty acid (2). This adjustment clearly falls within the general competence of those skilled in the art.

Preferably, the organic base is present in an amount sufficient to neutralize some or all of the carboxylic functions of the fatty acid(s) (2) comprising from 14 to less than 20 carbon atoms. In one preferred embodiment, the amount of base is such that it is capable of neutralizing all the acid functions of the fatty acid (2).

For example, the composition according to the invention may comprise at least 0.1% by weight, better still at least 0.15% by weight, of base, relative to the total weight of the composition.

According to one preferred embodiment of the invention, the base is present in a content ranging from 0.2% to 3.0% by weight, preferably from 0.3% to 2.0% by weight of organic base(s), in particular of aminomethylpropanediol, relative to the total weight of the composition according to the invention.

According to one particular embodiment of the invention, an ionic surfactant results from the total neutralization of stearic acid by an aminomethylpropanediol.

The fatty acid (2) and the organic base (3) making up the neutralized ionic surfactant according to the invention can be introduced into the composition in the form of one and the same commercial material, or one after the other in the form of two distinct commercial materials. Preferably, the fatty acid (2) and the organic base (3) will be introduced into the composition in the form of two distinct commercial materials.

Fatty Alcohol (4)

The compositions according to the invention also comprise at least one fatty alcohol. A composition can therefore comprise a single fatty alcohol according to the invention or several distinct fatty alcohols.

If several distinct fatty alcohols are present, they can be added separately during the preparation of the composition and the mixture thereof can then be formed in situ. They can also be used in the form of a mixture which is already commercially available and in which the weight proportion and the degree of purity of each of the fatty alcohols are controlled. In other words, the composition of these mixtures is faithfully reproducible, as opposed to mixtures of fatty alcohols generated via synthesis from starting materials derived from complex mixtures.

The fatty alcohol(s) is (are) in particular chosen from linear or branched, saturated or unsaturated $C_{14}$-$C_{30}$, preferably $C_{14}$-$C_{24}$, and even better still $C_{14}$-$C_{20}$, fatty alcohols.

The fatty alcohol(s) is (are) in particular chosen from linear and saturated $C_{14}$-$C_{30}$ fatty alcohols, preferably linear and saturated $C_{14}$-$C_{24}$ fatty alcohols, and better still linear and saturated $C_{14}$-$C_{20}$ fatty alcohols.

According to one particularly preferred embodiment, the fatty alcohol is in the form of a mixture of several different fatty alcohols, and preferably is a mixture of several linear and saturated $C_{14}$-$C_{30}$, better still $C_{14}$-$C_{24}$, even better still $C_{14}$-$C_{20}$, fatty alcohols.

Preferably, the fatty alcohol according to the invention is chosen from ($C_{16}$) cetyl alcohol, ($C_{18}$) stearyl alcohol and mixtures thereof (also known as "cetearyl alcohol"). Preferentially, the fatty alcohol according to the invention is a mixture of cetyl alcohol and stearyl alcohol. Such a mixture is in particular sold under the name Lannette O OR/MB by the company BASF.

According to one preferred embodiment, the fatty alcohol is solid at ambient temperature.

The fatty alcohol is present in the compositions of the invention in amounts ranging from 1.0% to 20.0% by weight, relative to the total weight of the composition, preferably from 2.0% to 15.0% by weight and even more particularly from 3.0% to 10.0% by weight relative to the total weight of the composition.

Water (5)

A composition according to the invention comprises water.

In particular, a composition according to the invention comprises at least 30.0% by weight, better still at least 40.0% by weight, or even a content of from 50% to 60% by weight of water, relative to the total weight of the composition.

In one preferred embodiment of the invention, the composition according to the invention comprises:
(1) at least one linear fatty acid monoester of formula (I):

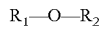

in which $R_1$ and $R_2$ are linear and saturated and have, independently of one another, a number of carbon atoms ranging from 20 to 24, with $R_1$ representing an acyl radical, and $R_2$ representing an alkyl radical, and
(2) at least one fatty acid chosen from stearic acid, palmitic acid and mixtures thereof,
(3) at least aminomethylpropanediol,
(4) at least one linear and saturated fatty alcohol chosen from those which are $C_{14}$-$C_{20}$, and
(5) water.

In yet another particularly preferred embodiment, the composition according to the invention comprises:
(1) at least one linear fatty acid monoester of formula (I):

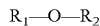

in which $R_1$ and $R_2$ are linear and saturated and have, independently of one another, a number of carbon atoms ranging from 20 to 24, with $R_1$ representing an acyl radical, and $R_2$ representing an alkyl radical, and
(2) at least stearic acid as fatty acid,
(3) at least aminomethylpropanediol,
(4) at least a mixture of cetyl and stearyl alcohol as fatty alcohol, and
(5) water.

In yet another particularly preferred embodiment, the composition according to the invention comprises:
(1) at least behenyl behenate as linear fatty acid monoester of formula (I), and
(2) at least one fatty acid chosen from stearic acid, palmitic acid and mixtures thereof,
(3) at least aminomethylpropanediol,
(4) at least a mixture of cetyl and stearyl alcohol as fatty alcohol, and
(5) water.

In yet another particularly preferred embodiment, the composition according to the invention comprises:
(1) at least behenyl behenate as linear fatty acid monoester of formula (I), and
(2) at least stearic acid as fatty acid,
(3) at least aminomethylpropanediol,
(4) at least linear and saturated fatty alcohol chosen from those which are $C_{14}$-$C_{20}$, and
(5) water.

In yet another particularly preferred embodiment, the composition according to the invention comprises:
(1) at least behenyl behenate as linear fatty acid monoester of formula (I), and
(2) at least stearic acid as fatty acid,
(3) at least aminomethylpropanediol,
(4) at least a mixture of cetyl and stearyl alcohol as fatty alcohol, and
(5) water.

In yet another particularly preferred embodiment, the composition according to the invention comprises:
(1) at least behenyl behenate as linear fatty acid monoester of formula (I), and
(2) at least stearic acid as fatty acid,
(3) at least aminomethylpropanediol,
(4) at least a mixture of cetyl and stearyl alcohol as fatty alcohol, and
(5) water,
at least one semi-crystalline organic polymer, preferably chosen from alkyl methacrylates, preferably containing at least one poly(behenyl acrylate).

In yet another particularly preferred embodiment, the composition according to the invention comprises:
(1) at least behenyl behenate as linear fatty acid monoester of formula (I), and
(2) at least stearic acid as fatty acid,
(3) at least aminomethylpropanediol,
(4) at least a mixture of cetyl and stearyl alcohol as fatty alcohol, and
(5) water,
at least one non-silicone polymeric gelling agent comprising hydrogen bonds, chosen from polyamides, preferably being the ethylenediamine/stearyl dimer dilinoleate copolymer.

Other Components

In addition to the abovementioned compounds, a composition according to the invention may of course comprise secondary ingredients.

a) Waxes

Thus, a composition according to the invention may also comprise a wax.

However, with regard to the objectives targeted by the present invention, the compositions according to the invention preferably comprise a reduced amount of wax and in particular less than 5% by weight, or even less than 3% by weight of waxes, relative to the total weight of said compositions.

As specified in the preamble, for the purposes of the invention, the term "waxes" is intended to mean lipophilic compounds, which are solid at ambient temperature (20° C.) and at atmospheric pressure (760 mmHg), with a reversible solid/liquid change of state, which have a melting point of greater than or equal to 40° C., which may range up to 120° C.

It is recalled that, for the purposes of the invention, the waxes to which the abovementioned amount limitation relates are distinct from those capable of being embodied by the component which is a monoester of fatty acid(s) (1) and/or the fatty alcohol (4) component required according to the invention.

This limitation relates more particularly to waxes made up of complex mixtures which are in particular described in the document Ullmann's Encyclopedia of Industrial Chemistry 2015, Wiley-VCH Verlag GmbH & Co. KGaA.

Such waxes may in particular be natural, but may also be synthetic.

The term "natural" wax is intended to denote any wax which preexists naturally or which can be converted, extracted or purified from natural compounds which exist naturally.

Among natural waxes, mention may in particular be made of waxes termed fossil waxes, including those of petroleum origin, such as ozokerite, pyropissite, macrocrystalline waxes, also known as paraffins—including crude or gatsch waxes, gatsch raffinates, de-oiled gatsch, soft waxes, semi-refined waxes, filtered waxes, refined waxes—and microcrystalline waxes, termed microwaxes, including bright stock gatsch. The fossil waxes also contain lignite, also known as montan wax, or peat wax.

As natural waxes other than fossil waxes, mention may be made of animal and plant waxes.

As examples of plant waxes, mention may be made of carnauba wax, candelilla wax, ouricury wax, sugarcane wax, jojob waxa, Trithrinax *campestris* wax, raffia wax, alfalfa wax, wax extracted from Douglas fir, sisal wax, flax wax, cotton wax, Batavia dammar wax, cereal wax, tea wax, coffee wax, rice wax, palm wax, Japan wax, mixtures thereof and derivatives thereof.

As examples of animal waxes, mention may be made of beeswax, Ghedda wax, shellac, Chinese wax, lanolin, also known as wool wax, mixtures thereof and derivatives thereof.

These waxes are generally multicomponent. For example, natural beeswax is composed of approximately 70% of esters for the majority of monoesters (of fatty acid and of fatty alcohol), but also of hydroxy esters, of diesters and triesters and esters of sterols, and also of long-chain linear hydrocarbons, of free acids and of free alcohols. For obvious reasons, the weight portion of their ingredients and their degree of purity are difficult to guarantee from one production batch to another.

The term "synthetic" wax is intended to denote waxes of which the synthesis requires one or more chemical reactions carried out by a human being.

Among the synthetic waxes, semi-synthetic waxes and totally synthetic waxes can be distinguished. Synthetic waxes may be waxes obtained by means of a Fischer-Tropsch process, constituted for example of paraffins with a number of carbon atoms ranging from 20 to 50 or waxes of polyolefins, for example homopolymers or copolymers of ethylene, of propene or butene, or even longer-chain α-olefins. The latter can be obtained by thermomechanical degradation of polyethylene plastic, by the Ziegler process, by high-pressure processes, or else via processes catalyzed by metallocene species. These waxes may be crystallizable, partially crystallizable or amorphous. The abovementioned synthetic waxes are generally non-polar and can be chemically treated to obtain polar waxes, for example by one or more of the following reactions: air oxidation, grafting, esterification, neutralization by metal soaps, amidation, direct copolymerizations or addition reactions.

Again in that case, their composition may be constituted of a mixture of ingredients since the fatty-chain lengths are not well defined, thus forming a mixture of compounds having different fatty-chain lengths and for which it is difficult for manufacturers to guarantee perfect reproducibility from one production batch to another.

Consequently, the compositions according to the invention advantageously comprise less than 5% by weight, preferably less than 3% by weight of waxes, in particular of multicomponent natural or synthetic wax, relative to the total weight of the composition.

For the purposes of the invention, a multicomponent wax denotes a wax constituted of a mixture of several ingredients, either such that it exists naturally like natural waxes, or such that it is formed during the process of industrial synthesis of these materials.

In one particularly preferred embodiment of the invention, the composition is free of these waxes, in particular multicomponent natural or synthetic wax.

As specified above, the preferred texturing compounds according to the invention are by contrast and advantageously synthetic, single-component compounds, which are thus available in a form purified to more than 99%, like the compound (1) required according to the invention.

b) Other Surfactants

The composition according to the invention can comprise surfactants other than that formed by the neutralization of a fatty acid having from 14 carbon atoms to less than 20 carbon atoms (2) by the organic base (3), as co-surfactants.

However, according to one preferred embodiment of the invention, the composition comprises less than 5.0% by weight, preferably less than 2.0% by weight, relative to the total weight of the composition, of non-ionic surfactants, and in particular of non-ionic surfactants with an HLB, measured at 25° C., of greater than or equal to 7.

The term "HLB" (Hydrophilic Lipophilic Balance) is well known to those skilled in the art, and denotes the hydrophilic-lipophilic balance of a surfactant determined at 25° C. in the Griffin sense. The term "hydrophilic-lipophilic balance (HLB)" is intended to mean the equilibrium between the size and the strength of the hydrophilic group and the size and the strength of the lipophilic group of the surfactant. The HLB value according to Griffin is defined in J. Soc. Cosm. Chem. 1954 (volume 5), pages 249-256.

In one particularly preferred embodiment of the invention, the composition is free of non-ionic surfactants with an HLB of greater than or equal to 7.

c) Hydrophilic Film-Forming Polymer(s)

A composition according to the invention may preferably comprise at least one hydrophilic film-forming polymer.

For the purposes of the present invention, the term "hydrophilic polymer" is intended to mean a water-soluble polymer.

For the purposes of the present invention, the term "water-soluble polymer" is intended to mean a polymer which, when introduced into water at a concentration equal to 1%, gives a macroscopically homogeneous solution of which the light transmittance, at a wavelength equal to 500 nm, through a sample 1 cm thick, is at least 10%.

For the purposes of the present invention, the term "film-forming polymer" is intended to mean a polymer that is capable, by itself or in the presence of an auxiliary film-forming agent, of forming a macroscopically continuous deposit, and preferably a cohesive deposit, and even better still a deposit of which the cohesion and mechanical properties are such that said deposit can be isolated and manipulated individually, for example when said deposit is prepared by pouring onto a non-stick surface such as a teflonated or siliconated surface.

For the purposes of the invention, a hydrophilic film-forming polymer that is particularly advantageous is a (poly)vinylpyrrolidone hydrophilic polymer.

A (poly)vinylpyrrolidone hydrophilic polymer suitable for the invention may have a weight-average molecular weight, Mw, ranging from 1500 to 500 000 g/mol.

A composition according to the invention comprises a total solid content of (poly)vinylpyrrolidone hydrophilic polymer(s) of greater than or equal to 0.5% by weight, preferably greater than or equal to 1.0% by weight, more preferentially greater than or equal to 1.5% by weight, relative to the total weight of the composition.

The composition according to the invention preferably comprises from 0.1% to 15.0% by weight, preferably from 0.5% to 10.0% by weight, better still from 1.0% to 8.0% by weight of hydrophilic film-forming polymer(s), relative to the total weight of the composition.

Preferably, the (poly)vinylpyrrolidone hydrophilic polymer(s) in accordance with the invention is (are) linear.

In particular, the (poly)vinylpyrrolidone hydrophilic polymer(s) in accordance with the invention is (are) chosen from statistical polymers, block copolymers, and a mixture thereof. The term "block copolymer" is intended to mean a polymer comprising at least two different blocks and preferably at least three different blocks.

The (poly)vinylpyrrolidone hydrophilic polymer(s) is (are) chosen from:
 (poly)vinylpyrrolidone homopolymers;
 copolymers of (poly)vinylpyrrolidone/(poly)vinyl acetate, esters,
 copolymers of (poly)vinylpyrrolidone/(meth)acrylic, salts thereof, and a mixture thereof.

As (poly)vinylpyrrolidone homopolymers, mention may for example be made of:
 the polyvinylpyrrolidone (2500 g/mol) sold under the trade name Kollidon 17 PF by the company BASF,
 the polyvinylpyrrolidone sold under the trade name Luviskol K 30 Powder by the company BASF or else sold under the trade name PVP K 30L by the company ISP (Ashland),
 the polyvinylpyrrolidone sold under the trade name PVP K 90 by the company ISP (Ashland)

As (poly)vinylpyrrolidone/(poly)vinyl acetate copolymers, mention may for example be made of the vinylpyrrolidone/vinyl acetate (60/40) copolymer sold under the trade name Luviskol VA 64 Powder by the company BASF.

d) Liquid Fatty Phase

A composition according to the invention may also comprise a liquid fatty phase.

Such a liquid fatty phase is an organic phase that is liquid at ambient temperature (20° C.) and at atmospheric pressure (760 mmHg), non-aqueous and water-immiscible.

The liquid fatty phase may contain a non-volatile oil chosen from polar oils and non-polar oils, and mixtures thereof.

A composition of the invention may comprise from 1.0% to 20.0% by weight, from 2.0% to 12.0% by weight and preferentially from 2.0% to 8.0% by weight of non-volatile oil, relative to the total weight of the composition.

A composition according to the invention generally comprises less than 5.0% by weight, preferably less than 2.0% by weight of volatile oil(s), relative to the total weight of the composition. In one particularly preferred embodiment of the invention, the composition is free of volatile oils.

The term "volatile oil" is intended to mean an oil that can evaporate on contact with the skin in less than one hour, at ambient temperature (20° C.) and atmospheric pressure (760 mmHg). More specifically, a volatile oil has an evaporation rate ranging from 0.01 to 200 mg/cm$^2$·min.

e) Colorant

A composition according to the invention, and in particular those intended for makeup, generally comprises at least one colorant such as pulverulent colorants, liposoluble dyes or water-soluble dyes.

The pulverulent colorants can be chosen from pigments and pearlescent agents.

The pigments may be white or coloured, mineral and/or organic, and coated or uncoated. Mention may be made, among mineral pigments, of titanium dioxide, optionally surface treated, zirconium, zinc or cerium oxides, and also iron or chromium oxides, manganese violet, ultramarine blue, chromium hydrate and ferric blue. Among the organic pigments that may be mentioned are carbon black, pigments of D & C type and lakes based on cochineal carmine, on barium, strontium, calcium or aluminium.

The pearlescent agents may be chosen from white pearlescent pigments such as mica coated with titanium or with bismuth oxychloride, coloured pearlescent pigments such as titanium mica with iron oxides, titanium mica especially with ferric blue or chromium oxide, titanium mica with an organic pigment of the abovementioned type, and also pearlescent pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the composition according to the invention comprises a pulverulent colorant, preferably of pigment type, in particular metal oxides.

Preferably, said colorant is present in the composition in a content ranging from 2.0% to 25.0% by weight, preferably from 3.0% to 20.0%, more particularly from 4.0% to 15.0% by weight, relative to the total weight of the composition.

f) Cosmetic Active Agents

As cosmetic active agents that may be used in the compositions according to the invention, mention may be made in particular of antioxidants, preservatives, fragrances, neutralizers, cosmetic active agents, for instance emollients, vitamins and screening agents, in particular sunscreens, and mixtures thereof.

These additives may be present in the composition in a content ranging from 0.01% to 15.0% of the total weight of the composition.

Of course, those skilled in the art will take care to choose the optional additional additives and/or their amounts in such a way that the advantageous properties of the composition according to the invention are not, or are not substantially, detrimentally affected by the envisaged addition.

g) Semi-Crystalline Polymer

A composition according to the invention may also comprise a semi-crystalline polymer.

For example, a composition according to the invention may comprise at least 3.0% by weight and preferably at least 4.0% by weight, or even from 5.0% to 12.0% by total weight of said semi-crystalline polymer, relative to the total weight of the composition.

For the purposes of the invention, the term "polymer" is intended to mean compounds comprising at least two repeating units, preferably at least three repeating units and more especially at least ten repeating units.

For the purposes of the invention, the term "semi-crystalline polymer" is intended to mean polymers comprising a crystallizable portion and an amorphous portion and having a first-order reversible change of phase temperature, in particular of melting (solid-liquid transition). The crystallizable portion is preferably a chain that is lateral (or a chain that is pendent) relative to the backbone.

Besides the crystallizable chains or blocks, the blocks of the polymers are amorphous.

For the purposes of the invention, the term "crystallizable chain or block" is intended to mean a chain or block which, if it were alone, would change from the amorphous state to the crystalline state reversibly, depending on whether the temperature is above or below the melting point. For the purposes of the invention, a chain is a group of atoms, which are pendent or lateral relative to the polymer backbone.

When the crystallizable portion is a chain that is pendent relative to the backbone, the semi-crystalline polymer may be a homopolymer or a copolymer.

Preferably, the semi-crystalline polymer has an organic structure.

The term "organic compound" or "having an organic structure" is intended to mean compounds containing carbon atoms and hydrogen atoms and optionally heteroatoms such as S, O, N or P, alone or in combination.

The semi-crystalline polymer(s) optionally present according to the invention are solids at ambient temperature (25° C.) and atmospheric pressure (760 mmHg), the melting point of which is greater than or equal to 30° C.

The melting point values correspond to the melting point measured using a differential scanning calorimeter (D.S.C.) such as the calorimeter sold under the name DSC 30 by the company Mettler, with a temperature rise of 5° C. or 10° C. per minute. The melting point in question is the point corresponding to the temperature of the most endothermic peak in the thermogram.

According to one particular embodiment, the semi-crystalline polymer(s) that can be used in the composition of the invention have a melting point Mp of less than 95° C., preferably less than 85° C. The semi-crystalline polymer(s) can thus have a melting point Mp ranging from 30° C. to 95° C. and preferably from 40° C. to 85° C. This melting point is preferably a first-order change of state temperature.

Where appropriate, the semi-crystalline polymers are advantageously soluble in the fatty phase, especially to at least 1.0% by weight, at a temperature that is higher than their melting point.

Preferably, the polymer backbone of the semi-crystalline polymers is soluble in the fatty phase at a temperature above their melting point.

Preferably, the crystallizable blocks or chains of the semi-crystalline polymers represent at least 30% of the total weight of each polymer and better still at least 40%.

When the semi-crystalline polymers are present, and are with crystallizable blocks, they can be block or multiblock copolymers. They may be obtained by polymerizing a monomer bearing reactive (or ethylenic) double bonds or by polycondensation. When the semi-crystalline polymers are present and are polymers bearing crystallizable side chains, these side chains are advantageously in random or statistical form.

Preferably, the semi-crystalline polymers, if they are present, are of synthetic origin.

According to one preferred embodiment, the semi-crystalline polymer may be chosen from homopolymers and copolymers comprising units resulting from the polymerization of one or more monomers bearing crystallizable hydrophobic side chain(s).

The semi-crystalline polymers that can be used in the invention may be chosen in particular from homopolymers or copolymers, in particular those bearing at least one crystallizable side chain, such as those described in document U.S. Pat. No. 5,156,911.

In one preferred embodiment, the crystallizable side chain(s) are hydrophobic.

These homopolymers or copolymers can result:

from the polymerization, in particular the radical polymerization, of one or more monomers containing double bond(s) which is (are) reactive, or which is (are) ethylenic, with respect to a polymerization, namely a vinyl, (meth) acrylic or allylic group, from the polycondensation of one or more monomers bearing co-reactive groups (carboxylic acid, sulfonic acid, alcohol, amine or isocyanate), for instance polyesters, polyurethanes, polyethers or polyureas.

In general, the crystallizable units (chains or blocks) of semi-crystalline polymers that may be suitable for the invention originate from monomer(s) containing crystallizable block(s) or chain(s), used for manufacturing semi-crystalline polymers. These polymers, if they are present, are preferably chosen especially from homopolymers and copolymers resulting from the polymerization of at least one monomer containing crystallizable chain(s) that may be represented by the formula (II):

(II)

with M representing an atom of the polymer backbone, C representing a crystallizable group, and S representing a spacer, the crystallizable "—S—C" chains being hydrocarbon-based aliphatic or aromatic chains, comprising saturated or unsaturated, hydrocarbon-based alkyl chains, which are for example $C_{10}$-$C_{40}$, preferably $C_{10}$-$C_{30}$.

"C" represents in particular a linear or branched or cyclic $(CH_2)_n$ group, with n being an integer ranging from 10 to 40. Preferably, "C" is a linear group. Preferably, "S" and "C" are different.

When the crystallizable chains are hydrocarbon-based aliphatic chains, they comprise hydrocarbon-based alkyl chains containing at least 10 carbon atoms and not more than 40 carbon atoms and better still not more than 30 carbon atoms. They are in particular aliphatic chains or alkyl chains containing at least 10 carbon atoms, and they are preferably $C_{10}$-$C_{40}$, preferably $C_{10}$-$C_{30}$, alkyl chains.

Preferably, the crystallizable chains are hydrocarbon-based aliphatic $C_{10}$-$C_{30}$ chains.

As examples of semi-crystalline homopolymers or copolymers containing crystallizable chain(s) that are suitable for the invention, mention may be made of those resulting from the polymerization of one or more of the following monomers: saturated alkyl (meth)acrylates with the alkyl group being $C_{10}$-$C_{30}$, N-alkyl(meth)acrylamides with the alkyl group being $C_{10}$ to $C_{30}$, vinyl esters containing alkyl chains with the alkyl group being $C_{10}$ to $C_{30}$, vinyl ethers containing alkyl chains with the alkyl group being $C_{10}$ to $C_{30}$, $C_{10}$ to $C_{30}$ alpha-olefins such as, for example, octadecene, para-alkylstyrenes with an alkyl group containing from 10 to 30 carbon atoms, and mixtures thereof.

When the polymers result from a polycondensation, the hydrocarbon-based crystallizable chains as defined above are borne by a monomer that may be a diacid, a diol, a diamine or a diisocyanate.

When the semi-crystalline polymers optionally present in the composition of the invention are copolymers, they additionally contain from 0 to 50% of groups Y which is a polar monomer, a non-polar monomer or a mixture of the two.

When Y is a polar monomer, it is either a monomer bearing polyoxyalkylene (in particular oxyethylene and/or oxypropylene) groups, a hydroxyalkyl (meth)acrylate, such as hydroxy ethyl acrylate, (meth)acrylamide, an N-alkyl (meth)acrylamide, an NN-dialkyl(meth)acrylamide, for instance NN-diisopropylacrylamide or N-vinylpyrolidone (NVP), N-vinylcaprolactam, or a monomer bearing at least one carboxylic acid group, such as (meth)acrylic, crotonic, itaconic, maleic or fumaric acids, or bearing a carboxylic acid anhydride group, such as maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a $C_1$ to $C_{10}$ alkyl group, for instance α-methylstyrene, or a macromonomer of the polyorganosiloxane type comprising a vinyl unsaturation.

Preferably, the semi-crystalline polymers containing crystallizable side chain(s) are alkyl (meth)acrylate or alkyl (meth)acrylamide homopolymers with an alkyl group as defined above, and in particular of $C_{10}$-$C_{30}$, copolymers of these monomers with a hydrophilic monomer preferably of different nature from (meth)acrylic acid, for instance N-vinylpyrrolidone or hydroxyethyl (meth)acrylate, and mixtures thereof.

It is also possible to use the semi-crystalline polymers obtained by copolymerization of behenyl acrylate and of acrylic acid or of N-vinylpyrrolidone, as described in document U.S. Pat. No. 5,519,063.

Advantageously, the semi-crystalline polymer(s) containing crystallizable side chain(s) have a weight-average molecular weight Mw ranging from 5000 g/mol to 1 000 000 g/mol, preferably from 10 000 g/mol to 800 000 g/mol, preferentially from 15 000 g/mol to 500 000 g/mol, and more preferably from 80 000 g/mol to 200 000 g/mol.

According to one particular embodiment of the invention, a semi-crystalline polymer may be chosen from homopolymers and copolymers resulting from the polymerization of at least one monomer containing crystallizable side chain(s) chosen from saturated $C_{10}$ to $C_{30}$ alkyl (meth)acrylates, which may be represented by the formula below:

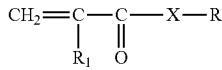

in which $R_1$ is H or $CH_3$, R represents a $C_{10}$ to $C_{30}$ alkyl group and X represents O.

According to one more particular embodiment of the invention, a semi-crystalline polymer results from the polymerization of monomers containing crystallizable side chain(s), chosen from saturated $C_{10}$ to $C_{30}$ alkyl (meth) acrylates.

The semi-crystalline polymers comprising crystallizable side chains can be chosen from the copolymers resulting from the copolymerization of acrylic acid and $C_{10}$ to $C_{30}$ alkyl (meth)acrylate, in particular such as those described in U.S. Pat. No. 5,156,911.

The semi-crystalline polymers may in particular be those described in Examples 3, 4, 5, 7 and 9 of U.S. Pat. No. 5,156,911, and more particularly those obtained by the copolymerization:
of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and of polyoctadecyl (meth)acrylate in a 2.5/97.5 ratio.

As a particular example of a semi-crystalline polymer that may be used in the composition according to the invention, mention may be made of the Intelimer® products from the company Landec described in the brochure "Intelimer® polymers", Landec IP22 (Rev. 4-97). These polymers are in solid form at ambient temperature (25° C.). They bear crystallizable side chains and have the preceding formula (II). They are poly($C_{10}$-$C_{30}$)alkyl acrylates, which are particularly suitable as semi-crystalline polymers that may be included in a composition in accordance with the present invention.

According to one particularly preferred embodiment of the invention, the semi-crystalline polymer(s) optionally present in the invention is (are) derived from a monomer containing a crystallizable chain, chosen from saturated $C_{10}$ to $C_{30}$ alkyl (meth)acrylates and more particularly from poly(stearyl acrylate)s, poly(behenyl acrylate)s, and mixtures thereof.

Preferably, the semi-crystalline polymers suitable for the invention are in particular poly(stearyl acrylate), in particular the product sold under the name Intelimer® IPA 13-1, from the company Air Products and Chemicals or Landec, which is a poly(stearyl acrylate) of which the melting point is equal to 49° C., or poly(behenyl acrylate), sold under the name Intelimer® IPA 13-6, from the company Air Products and Chemicals or Landec, which is a poly(behenyl acrylate) of which the melting point is equal to 65° C.

According to one particularly preferred embodiment, the semi-crystalline polymer may be at least one poly(behenyl acrylate).

Examples of homopolymers or copolymers suitable as semi-crystalline polymers for the invention preferably comprise from 50% to 100% by weight of units resulting from the polymerization of one or more monomers bearing a crystallizable hydrophobic side chain.

h) Non-Silicone Polymeric Gelling Agent Comprising Hydrogen Bonds

A composition according to the invention may also comprise a non-silicon polymeric gelling agent comprising hydrogen bonds.

For example, a composition according to the invention may comprise at least 3.0% by weight and preferably at least 4.0% by weight, or even from 5.0% to 12.0% by total weight of said non-silicone polymeric gelling polymer comprising hydrogen bonds, relative to the total weight of the composition.

For the purposes of the present invention, the term "non-silicone" is intended to specify that the polymer does not contain a silicon atom.

As representatives of non-silicone polymeric gelling agents comprising hydrogen bonds that are suitable for the invention, mention may be made most particularly of polyamides, better still hydrocarbon-based polyamides.

The term "hydrocarbon-based polyamide" is intended to mean a polyamide formed essentially of, or even constituted of, carbon atoms, hydrogen atoms, oxygen atoms and nitrogen atoms, and not containing a silicon or fluorine atom, the compound having at least 2 repeating amide units, preferably at least 3 repeating amide units and even better still 10 repeating amide units. It may contain alcohol, ester, ether, carboxylic acid, amine and/or amide groups.

Advantageously, a polyamide that may be suitable for the invention has a weight-average molecular weight of less than 100 000 g/mol, especially ranging from 1000 to 100 000 g/mol, in particular less than 50 000 g/mol, especially ranging from 1000 to 50 000 g/mol, and more particularly ranging from 1000 to 30 000 g/mol, preferably from 2000 to 20 000 g/mol and better still from 2000 to 10 000 g/mol.

This polyamide is preferably insoluble in water, especially at 25° C.

According to a first embodiment of the invention, the polyamide that may be used is a polyamide of formula (III):

$$X \!\!-\!\!\!\left[\!\!\begin{array}{c}C\\\|\\O\end{array}\!\!-\!R_2\!-\!\!\begin{array}{c}C\\\|\\O\end{array}\!\!-\!NH\!-\!R_3\!-\!NH\!\!\right]_{\!\!n}\!\!\!-\!\!\begin{array}{c}C\\\|\\O\end{array}\!\!-\!R_2\!-\!\!\begin{array}{c}C\\\|\\O\end{array}\!\!-\!X \qquad (III)$$

in which X represents a group $-N(R_1)_2$ or a group $-OR_1$ with each $R_1$ being a linear or branched $C_8$ to $C_{22}$ alkyl radical and possibly being identical or different from one another, $R_2$ is a $C_{28}$-$C_{42}$ diacid dimer residue, $R_3$ is an ethylenediamine radical and n ranges from 2 to 5; and mixtures thereof.

According to a first variant, the polyamide may be a polyamide of formula (III) with an amide end group, in which X represents a group $-N(R_1)_2$ with each $R_1$ being a linear or branched $C_8$ to $C_{22}$ alkyl radical which may be identical or different from one another, $R_2$ is a $C_{28}$-$C_{42}$ diacid dimer residue, $R_3$ is an ethylenediamine radical and n ranges from 2 to 5.

According to a second variant, the hydrocarbon-based polyamide may be a polyamide with an ester end group of formula (III) in which X represents a group $-OR_1$ with each $R_1$ being a linear or branched $C_8$ to $C_{22}$, preferably $C_{16}$ to $C_{22}$, alkyl radical which may be identical or different from one another, $R_2$ is a $C_{28}$-$C_{42}$ diacid dimer residue, $R_3$ is an ethylenediamine radical and n ranges from 2 to 5.

As representatives of these polyamides with an ester end group, mention may in particular be made of the commercial products sold by the company Arizona Chemical under the names Uniclear 80 and Uniclear 100 or else Uniclear 80 V, Uniclear 100 V and Uniclear 100 VG, or the company Croda under the name Oleocraft, the INCI name of which is ethylenediamine/stearyl dimer dilinoleate copolymer.

According to one embodiment, the invention comprises at least one non-silicone polymeric gelling agent comprising hydrogen bonds, preferably a polyamide, in particular an ethylenediamine/stearyl dimer dilinoleate copolymer, having the INCI name ethylenediamine/stearyl dimer dilinoleate copolymer.

Of course, a composition according to the invention may comprise one or more polymeric gelling agents comprising hydrogen bonds.

In particular, it may comprise a mixture of polyamides such as those described above.

Physical Characteristics
Solid Content

The composition according to the invention advantageously has a solid content at least equal to 42.0% by weight, preferably at least 44.0% by weight or even from 45.0% to 60.0% by weight, relative to the total weight of the composition.

For the purposes of the present invention, the "solid content" denotes the content of non-volatile matter.

The amount of solid content (abbreviated as SC) of a composition according to the invention is measured using a commercial halogen desiccator Halogen Moisture Analyzer HR 73 from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal cup, which is placed in the halogen desiccator mentioned above. The sample is then subjected to a temperature of 105° C. until a constant weight is obtained. The wet weight of the sample, corresponding to its initial weight, and the dry weight of the sample, corresponding to its weight after halogen heating, are measured using a precision balance.

The experimental error associated with the measurement is of the order of plus or minus 2%.

The solid content is calculated in the following manner:

Solid content(expressed as weight percentage)=100× (dry weight/wet weight).

Viscosity

A composition according to the invention is advantageously creamy at an ambient temperature of 20° C.

It is characterized by a viscosity of less than 40 Pa·s, or even preferably less than 35 Pa·s, or even less than 30 Pa·s, measured at an ambient temperature of 20° C. using an RM100® Rheomat.

Preferably, the viscosity of the compositions according to the invention is between 2.0 and 40.0 Pa·s, or even preferably between 2.0 and 35.0 Pa·s, more particularly between 2.0 and 30.0 Pa·s, measured at the ambient temperature of 20° C. using an RM100® Rheomat.

Such a viscosity is particularly advantageous since it is the most suitable for the device for applying mascara and since it enables easy use for the consumer for a charging result.

The composition may be produced via the known processes generally used in the cosmetics field.

The composition used according to the invention may be a makeup composition, a makeup base, in particular for keratin fibres, or base coat, a composition to be applied onto makeup, also known as topcoat, or else a composition for treating keratin fibres.

More especially, the composition according to the invention is a mascara.

Such compositions are especially prepared according to the general knowledge of those skilled in the art.

The expressions "between . . . and . . . " and "ranging from . . . to . . . " should be understood as being inclusive of the limits, unless otherwise specified.

In the description and the examples, the percentages are percentages by weight, unless otherwise indicated. The percentages are thus given by weight relative to the total weight of the composition. The ingredients are mixed in the order and under conditions that are readily determined by those skilled in the art.

The invention will now be described by means of examples which are present purely for illustrative purposes and should not be interpreted as examples that limit the invention.

EXAMPLES

Example 1

Compositions of mascara type, in accordance with the invention (Composition 1) or not in accordance with the invention (Composition 2) are prepared as described below.

Preparation of Phase A

The starting materials were carefully weighed out beforehand using a balance (precision=0.01 g). The ingredients of phase A were melted in a jacketed heating pan in which circulates an oil of which the temperature is controlled by means of a thermostatic oil bath. The setpoint temperature was fixed at 90° C. After total melting, the pigment was introduced with stirring using a Rayneri blender. Stirring was maintained until a homogeneous preparation was obtained.

Preparation of Phase B

The water was preheated in an electric kettle to 95° C. The preservatives and the organic base were introduced into the water in a beaker at a temperature of 80° C. with stirring using a Rayneri blender.

Emulsification of Phases A and B

Phase B was poured into phase A with stirring for 5 minutes at 90° C. using a Rayneri blender. Phase A+B was then cooled to ambient temperature with stirring.

End of Formulation

The mascara thus obtained was transferred into a closed container to prevent it from drying out on contact with air. After 24 h, the macroscopic homogeneity of the sample and the state of dispersion of the fatty substances and of the pigment were evaluated under an optical microscope and the viscosity was measured

| | Commercial reference | INCI name | Composition 1 according to the invention | Composition 2 outside the invention |
|---|---|---|---|---|
| A | Lanette O OR/MB from BASF | CETEARYL ALCOHOL ($C_{16}$-$C_{18}$) | 4.00 | 4.00 |
| | Kester wax K-72 from Koster keunen | BEHENYL BEHENATE (compound (1)) | 21.00 | — |
| | SYNCHROWAX HRC-PA-(MH) from Croda | TRIBEHENIN | — | 21.00 |
| | Stearic acid 1850 from Southern Acids | STEARIC ACID (compound (2)) | 6.00 | 6.00 |
| | Sunpuro black iron oxide C33-7001 from Sun | IRON OXIDES | 8.00 | 8.00 |
| | Polyvinyl pyrrolydone K 30 Powder from BASF | POLYVINYL PYRROLYDONE | 2.00 | 2.00 |
| B | Protectol PE CO from BASF | PHENOXY-ETHANOL | 0.60 | 0.60 |
| | Cosvat L from KRAEBER | CHLORPHENESIN | 0.30 | 0.30 |
| | 199602 Hydrolite CG from Symrise | CAPRYLYL GLYCOL | 0.80 | 0.80 |
| | AMPD Ultra PC from Angus (Dow Corning) | AMINOMETHYL PROPANEDIOL (compound (3)) | 1.00 | 1.00 |
| | | WATER | qs 24 | qs 0.35 |
| | Viscosity at 24 H (in Pa · s) | | | |
| | Viscosity after 2 months at 45° C. (in Pa · s) | | 23.6 | 15.1 |

Composition 1 according to the invention comprising all of the required compounds demonstrates satisfactory stability properties. Conversely, Composition 2 outside the invention which comprises just one of the required compounds according to the invention, namely the ionic surfactant resulting from the neutralization of a fatty acid by an organic base, is not stable.

Furthermore, Composition 2 exhibits insufficient texturizing to be compatible with use as a mascara. Composition 1 according to the invention has, for its part, a satisfactory viscosity.

Example 2

A composition according to the invention (Composition 3) and a composition outside the invention (Composition 4) presented below were prepared according to the protocol set out in Example 1:

| | Commercial reference | INCI name | Composition 3 according to the invention | Composition 4 outside the invention |
|---|---|---|---|---|
| A | Lanette O OR/MB from BASF | CETEARYL ALCOHOL ($C_{16}$-$C_{18}$) (compound (4)) | 4.00 | 4.00 |
| | Kester wax K-72 from Koster keunen | Behenyl behenate ($C_{44}$) (compound (1)) | 15.00 | — |
| | Radia 7501 from Oleon | CETEARYL STEARATE ($C_{34}$) | — | 15.00 |
| | Intelimer IPA 13-6 Polymer from Air Products and Chemicals | POLY $C_{10}$-$C_{30}$ ALKYLACRYLATE ($C_{22}$) | 6.00 | 6.00 |
| | Stearic acid 1850 from Southern Acids | STEARIC ACID (compound (2)) | 6.00 | 6.00 |
| | Sunpuro black iron oxide C33-7001 from Sun | IRON OXIDES | 8.00 | 8.00 |
| | Polyvinyl pyrrolydone K 30 Powder from BASF | POLYVINYL PYRROLYDONE | 2.00 | 2.00 |
| | Protectol PE CO from BASF | PHENOXY-ETHANOL | 0.60 | 0.60 |
| | Cosvat L from KRAEBER | CHLORPHENESIN | 0.30 | 0.30 |
| B | 199602 Hydrolite CG from Symrise | CAPRYLYL GLYCOL | 0.80 | 0.80 |
| | AMPD Ultra PC from Angus (Dow Corning) | AMINOMETHYL PROPANEDIOL (compound (3)) | 1.00 | 1.00 |
| | | WATER (compound (5)) | qs | qs |
| | Viscosity at 24 H (in Pa · s) | | 7.3 | 18.9 |
| | Viscosity after 2 months at 45° C. (in Pa · s) | | 8 | Impossible to determine |

The stability of the two compositions was studied. Composition 3 according to the invention exhibits satisfactory properties in terms of stability. Conversely, Composition 4 outside the invention is not stable. The viscosity of this Composition 4 after storage for two months at a temperature of 45° C. is not even any longer measurable: the texture has become solid.

This difference in stability between the two compositions makes it possible to demonstrate the importance of incorporating a linear fatty acid monoester of formula (I) into the compositions according to the invention.

Example 3

Compositions 3 and 7 according to the invention and two compositions outside the invention (Compositions 5 and 6) presented below were prepared according to the protocol set out in Example 1:

and 6, outside the invention, are not stable. Indeed, the first composition is non-homogeneous to the naked eye, whereas the second exhibits phase separation.

Thus, it is demonstrated that Compositions 3 and 7 according to the invention, comprising a fatty acid comprising at least 14 carbon atoms, at least partially neutralized by an organic base, exhibit better stability and texture properties than Compositions 5 and 6 outside the invention, comprising other surfactant systems.

|   | Commercial reference | INCI name | Composition 3 according to the invention | Composition 5 outside the invention | Composition 6 outside the invention | Composition 7 according to the invention |
|---|---|---|---|---|---|---|
| A | Lanette O OR/MB from BASF | CETEARYL ALCOHOL ($C_{16}$-$C_{18}$) (compound (4)) | 4.00 | 4.00 | 4.00 | 4.00 |
|   | Kester wax K-72 from Koster keunen | BEHENYL BEHENATE ($C_{44}$) (compound (1)) | 15.00 | 15.00 | 15.00 | 15.00 |
|   | OLEOCRAFT LP-10-PA-(MV) from CRODA | ETHYLENEDIAMINE/ STEARYL DIMER DILINOLEATE COPOLYMER | — | — | — | 6.00 |
|   | Intelimer IPA 13-6 Polymer from Air Products and Chemicals | POLY $C_{10}$-$C_{30}$ ALKYLACRYLATE ($C_{22}$) | 6.00 | 6.00 | 6.00 | — |
|   | Stearic acid 1850 from Southern Acids | STEARIC ACID (compound (2)) | 6.00 | — | — | 6.00 |
|   | Brij S20-PA-(SG) from Croda | STEARETH-20 | — | 6.00 | — | — |
|   | Amisoft HS 11 from Ajinomoto | SODIUM STEAROYL GLUTAMATE | — | — | 6.00 | — |
|   | Sunpuro black iron oxide C33-7001 from Sun | IRON OXIDES | 8.00 | 8.00 | 8.00 | 8.00 |
|   | Polyvinyl pyrrolydone K 30 Powder from BASF | POLYVINYL PYRROLYDONE | 2.00 | 2.00 | 2.00 | 2.00 |
| B | Protectol PE CO from BASF | PHENOXYETH ANOL | 0.60 | 0.60 | 0.60 | 0.60 |
|   | Cosvat L from KRAEBER | CHLORPHENESIN | 0.30 | 0.30 | 0.30 | 0.30 |
|   | 199602 Hydrolite CG from Symrise | CAPRYLYL GLYCOL | 0.80 | 0.80 | 0.80 | 0.80 |
|   | AMPD Ultra PC from Angus (Dow Corning) | AMINOMETHYL PROPANEDIOL (compound (3)) | 1.00 | 1.00 | 1.00 | 1.00 |
|   |   | WATER (compound (5)) | qs | qs | qs | qs |

Compositions 3 and 7 are homogeneous and constitute fine emulsions: the dispersion of the fatty substances and of the pigments is homogeneous in the sample, whereas for Compositions 5 and 6 outside the invention, the dispersion of the fatty substances is non-homogeneous. Indeed, Composition 5, for its part, gives rise to a coarse emulsion comprising clumps of crystals, and Composition 6 also exhibits a coarse emulsion which contains large crystals.

The stability of the compositions was studied. Compositions 3 and 7 according to the invention exhibit satisfactory properties in terms of stability. Conversely, Compositions 5

The invention claimed is:

1. Composition, for caring for and/or making up keratin materials, comprising:
   (1) at least one linear fatty acid monoester of formula (I):

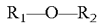

in which $R_1$ and $R_2$ are linear and saturated and have, independently of one another, a number of carbon atoms greater than or equal to 20, with $R_1$ representing an acyl radical, and $R_2$ representing an alkyl radical, and
   (2) at least one fatty acid having from 14 carbon atoms to less than 20 carbon atoms, (3) at least one organic base capable of at least partially neutralizing at least one fatty acid (2), and
(4) at least one fatty alcohol chosen from linear and saturated $C_{14}$-$C_{24}$ fatty alcohols, and
(5) water.

2. Composition according to claim 1, containing less than 5% by weight of waxes relative to the total weight of said composition.

3. Composition according to claim 1, in which $R_1$ and $R_2$ are, respectively, acyl and alkyl radicals having the same number of carbon atoms.

4. Composition according to claim 1, in which $R_1$ and $R_2$ are, respectively, acyl and alkyl radicals having a number of carbon atoms ranging from 20 to 30.

5. Composition according to claim 1, in which the linear fatty acid monoester (1) is chosen from arachidyl arachidate and behenyl behenate.

6. Composition according to claim 1, comprising at least 5.0% by weight of linear fatty acid monoester(s) (1) relative to the total weight of the composition.

7. Composition according to claim 1, in which the fatty acid(s) (2) is (are) chosen from linear fatty acids and saturated fatty acids, and mixtures thereof.

8. Composition according to claim 1, in which the fatty acid(s) (2) is (are) chosen from stearic acid and palmitic acid, and mixtures thereof.

9. Composition according to claim 1, comprising at least 3.0% by weight of fatty acid(s) (2) relative to the total weight of the composition.

10. Composition according to claim 1, in which the organic base (3) is chosen from triethanolamine, aminomethylpropanol and/or aminomethylpropanediol.

11. Composition according to claim 1, comprising at least 0.1% by weight of organic base (3), relative to the total weight of the composition.

12. Composition according to claim 1, comprising at least one fatty alcohol (4) chosen from ($C_{16}$) cetyl alcohol, ($C_{18}$) stearyl alcohol and mixtures thereof.

13. Composition according to claim 1, comprising at least from 1.0% to 20.0% by weight of fatty alcohol(s) (4), relative to the total weight of the composition.

14. Composition according to claim 1, comprising at least 30% by weight of water (5), relative to the total weight of said composition.

15. Composition according to claim 1, comprising less than 5.0% by weight of volatile oil(s), relative to the total weight of the composition.

16. Composition according to claim 1, comprising less than 5.0% by weight, relative to the total weight of the composition, of non-ionic surfactants with an HLB, measured at 25° C., of greater than or equal to 7.

17. Composition according to claim 1, comprising at least one (poly)vinylpyrrolidone hydrophilic polymer.

18. Composition according to claim 1, comprising at least one semi-crystalline polymer chosen from saturated $C_{10}$ to $C_{30}$ alkyl (meth)acrylates or mixtures thereof.

19. Composition according to claim 18, comprising at least 3.0% by weight of said semi-crystalline polymer, relative to the total weight of the composition.

20. Composition according to claim 1, further comprising at least one non-silicone polymeric gelling agent comprising hydrogen bonds.

21. Composition according to claim 20, comprising at least 3.0% by weight of said non-silicone polymeric gelling agent comprising hydrogen bonds, relative to the total weight of said composition.

22. Composition according to claim 1, comprising at least one pulverulent colorant.

23. Composition according to claim 1, comprising from 2.0% to 25.0% by weight of colorant, relative to the total weight of the composition.

24. Composition according to claim 1, having a solid content of at least 42.0% by weight relative to the total weight of said composition.

25. Process for caring for and/or making up keratin materials, comprising at least one step consisting in applying, to said keratin materials a composition according to claim 1.

* * * * *